(12) United States Patent
Kwak et al.

(10) Patent No.: US 10,080,542 B2
(45) Date of Patent: Sep. 25, 2018

(54) INFORMATION PROVIDING METHOD AND APPARATUS FOR ALIGNING X-RAY TUBE AND DETECTOR OF MOBILE X-RAY APPARATUS, AND WIRELESS DETECTOR

(71) Applicant: SAMSUNG ELECTRONICS CO., LTD., Suwon-si (KR)

(72) Inventors: Ho-seong Kwak, Hwaseong-si (KR); Sang-kyun Kang, Suwon-si (KR); Myeong-je Kim, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 1161 days.

(21) Appl. No.: 14/286,420

(22) Filed: May 23, 2014

(65) Prior Publication Data

US 2014/0376700 A1 Dec. 25, 2014

(30) Foreign Application Priority Data

Jun. 21, 2013 (KR) .................. 10-2013-0071952

(51) Int. Cl.
*A61B 6/00* (2006.01)
*G01B 7/30* (2006.01)

(52) U.S. Cl.
CPC ............ *A61B 6/587* (2013.01); *A61B 6/4291* (2013.01); *A61B 6/4405* (2013.01); *A61B 6/4452* (2013.01); *G01B 7/30* (2013.01)

(58) Field of Classification Search
CPC .............................. A61B 6/4452; A61B 6/587
See application file for complete search history.

(56) References Cited

U.S. PATENT DOCUMENTS

| 4,464,775 A | 8/1984 | Yamagishi |
| 5,651,043 A | 7/1997 | Tsuyuki et al. |

(Continued)

FOREIGN PATENT DOCUMENTS

| JP | 2012120564 A | 6/2012 |
| KR | 19980008175 A | 4/1998 |

OTHER PUBLICATIONS

Communication dated Jan. 28, 2016, issued by the Korean Intellectual Property Office in counterpart Korean Application No. 10-2013-0071952.

(Continued)

*Primary Examiner* — Dani Fox
(74) *Attorney, Agent, or Firm* — Sughrue Mion, PLLC

(57) ABSTRACT

Provided is an information providing method for aligning an X-ray tube and a detector of a mobile X-ray apparatus, the information providing method including: obtaining first angle information which relates to the X-ray tube by using a first angle measurement sensor which is connected to the X-ray tube; obtaining second angle information which relates to the detector by using a second angle measurement sensor which is connected to the detector; and outputting rotation information for guiding a rotation direction and a rotation angle of the X-ray tube or a rotation direction and a rotation angle of the detector such that an angle between a first plane which is set with respect to the X-ray tube and a second plane which is set with respect to the detector is within a predetermined angle range, based on the first angle information and the second angle information.

30 Claims, 13 Drawing Sheets

(56) References Cited

U.S. PATENT DOCUMENTS

| | | | |
|---|---|---|---|
| 5,873,826 A | 2/1999 | Gono et al. | |
| 7,581,884 B1 | 9/2009 | Barnes et al. | |
| 7,798,710 B1 | 9/2010 | Barnes et al. | |
| 2002/0150215 A1 | 10/2002 | Barnes et al. | |
| 2006/0109958 A1 | 5/2006 | Ertel et al. | |
| 2012/0039447 A1 | 2/2012 | Lalena et al. | |
| 2012/0230473 A1* | 9/2012 | Stagnitto | A61B 6/4291 378/205 |
| 2012/0307965 A1 | 12/2012 | Bothorel et al. | |

OTHER PUBLICATIONS

Communication, Issued by the International Searching Authority, dated Aug. 22, 2014, In counterpart International Application No. PCT/KR2014/004141.

\* cited by examiner

FIG. 12

ROTATION INFORMATION OF X-RAY TUBE

ROTATION DIRECTION
: COUNTERCLOCKWISE DIRECTION
ROTATION ANGLE : 30°

MOVEMENT INFORMATION OF X-RAY TUBE

X-AXIS DIRECTION : −10cm
Y-AXIS DIRECTION : +5cm
Z-AXIS DIRECTION : 0cm

INFORMATION PROVIDING METHOD AND APPARATUS FOR ALIGNING X-RAY TUBE AND DETECTOR OF MOBILE X-RAY APPARATUS, AND WIRELESS DETECTOR

RELATED APPLICATIONS

This application claims priority from Korean Patent Application No. 10-2013-0071952, filed on Jun. 21, 2013 in the Korean Intellectual Property Office, the disclosure of which is incorporated herein by reference in its entirety.

BACKGROUND

1. Field

One or more exemplary embodiments relate to an information providing method and apparatus for aligning an X-ray tube and a detector of a mobile X-ray apparatus that captures a medical image of an object, and a wireless detector.

2. Description of the Related Art

An X-ray apparatus is a medical image system which may be configured for obtaining an image of an inner structure of a human body by penetrating an x-ray through the human body. A medical image of an object may be conveniently and quickly obtained by using the X-ray apparatus, as compared to other medical image systems such as a magnetic resonance imaging (MRI) apparatus or a computed tomography (CT) apparatus. Accordingly, the X-ray apparatus is widely used to photograph a plain chest, a plain abdomen, a plain ossature, a plain pansinusitis, a plain neck soft tissue, or a breast.

Recently, a mobile X-ray apparatus has been suggested. The mobile X-ray apparatus may be very useful when photographing a patient who is difficult to move, but is generally characterized by a low medical image quality, as compared to a stationary X-ray apparatus. Accordingly, the medical image quality of the mobile X-ray apparatus needs to be improved.

SUMMARY

One or more exemplary embodiments provide a simple method of aligning an X-ray tube and a detector of a mobile X-ray apparatus in order to improve a quality of a medical image captured by the mobile X-ray apparatus.

According to one or more exemplary embodiments, an information providing method for aligning an X-ray tube and a detector of a mobile X-ray apparatus is provided, and the information providing method includes: obtaining first angle information which relates to the X-ray tube by using a first angle measurement sensor which is connected to the X-ray tube; obtaining second angle information which relates to the detector by using a second angle measurement sensor which is connected to the detector; and outputting rotation information which relates to guiding at least one from among a rotation direction and a rotation angle of the X-ray tube and a rotation direction and a rotation angle of the detector such that an angle between a first plane which is set with respect to the X-ray tube and a second plane which is set with respect to the detector is within a predetermined angle range, based on the obtained first angle information and the obtained second angle information.

Each of the first angle measurement sensor and the second angle measurement sensor may include at least one from among a gyro sensor, an acceleration sensor, and a geomagnetic sensor.

The obtaining the first angle information may include obtaining first angle information which indicates a rotated angle and a rotated direction of the first plane with respect to a first reference axis, and the obtaining the second angle information may include obtaining second angle information which indicates a rotated angle and a rotated direction of the second plane with respect to a second reference axis.

The information providing method may further include rotating at least one from among the X-ray tube and the detector based on the outputted rotation information.

The information providing method may further include: obtaining, from the detector, magnetic field intensity information which relates to a magnetic field which is emitted by the X-ray tube; determining a relative location with respect to the X-ray tube and the detector by using the obtained magnetic field intensity information; and outputting movement information which relates guiding at least one from among a movement location of the X-ray tube and a movement location of the detector such that a first axis which is set with respect to the X-ray tube intersects a predetermined region of the detector, based on the determined relative location with respect to the X-ray tube and the detector.

The information providing method may further include setting the first axis to be perpendicular to the first plane.

The obtaining the magnetic field intensity information may include obtaining at least one piece of magnetic field intensity information from at least one magnetic field sensor which is connected to the detector, and the determining the relative location with respect to the X-ray tube and the detector may include: comparing the obtained at least one piece of magnetic field intensity information with reference magnetic field intensity information; and determining the relative location with respect to the X-ray tube and the detector based on a result of the comparing.

The obtaining the magnetic field intensity information may include: obtaining, from a first magnetic field sensor which is connected to a first point of the detector, first direction magnetic field intensity information which relates to a first direction of the magnetic field which is emitted by the X-ray tube; and obtaining, from a second magnetic field sensor which is connected to a second point of the detector, second direction magnetic field intensity information which relates to a second direction of the magnetic field which is emitted by the X-ray tube, and the determining the relative location with respect to the X-ray tube and the detector may include determining the relative location with respect to the X-ray tube and the detector based on the obtained first direction magnetic field intensity information and the obtained second direction magnetic field intensity information.

The determining the relative location between the X-ray tube and the detector may further include comparing the obtained first direction magnetic field intensity information with first reference magnetic field intensity information and comparing the obtained second direction magnetic field intensity information with second reference magnetic field intensity information.

The obtaining the magnetic field intensity information may include obtaining, from a third magnetic field sensor which is connected to a third point of the detector, third direction magnetic field intensity information which relates to a third direction and fourth direction magnetic field intensity information which relates to a fourth direction of the magnetic field which is emitted by the X-ray tube, and the determining the relative location with respect to the X-ray tube and the detector may include determining the relative location with respect to the X-ray tube and the detector based on the obtained third direction magnetic field intensity information and the obtained fourth direction magnetic field intensity information.

The determining the relative location between the X-ray tube and the detector may include comparing the obtained third direction magnetic field intensity information with third reference magnetic field intensity information and comparing the obtained fourth direction magnetic field intensity information with fourth reference magnetic field intensity information.

The outputting may include displaying a first figure which corresponds to the X-ray tube on a display which is connected to the mobile X-ray apparatus based on the obtained first angle information, and displaying a second figure which corresponds to the detector on the display based on the obtained second angle information.

The information providing method may further include displaying a first figure which corresponds to the X-ray tube and a second figure which corresponds to the detector on a display which is connected to the mobile X-ray apparatus based on the determined relative location with respect to the X-ray tube and the detector.

According to one or more exemplary embodiments, an information providing method for aligning an X-ray tube and a detector of a mobile X-ray apparatus is provided, and the information providing method includes: obtaining, from the detector, magnetic field intensity information which relates to a magnetic field which is emitted by the X-ray tube; determining a relative location with respect to the X-ray tube and the detector by using the obtained magnetic field intensity information; and outputting movement information which relates to guiding at least one from among a movement location of the X-ray tube and a movement location of the detector such that a first axis which is set with respect to the X-ray tube intersects a predetermined region of the detector, based on the determined relative location with respect to the X-ray tube and the detector.

According to one or more exemplary embodiments, a method for providing location information to a mobile X-ray apparatus by using a wireless detector which is configured for detecting an X-ray which is emitted from an X-ray tube of the mobile X-ray apparatus is provided, and the method includes: obtaining at least one piece of magnetic field intensity information which relates to a magnetic field which is emitted by the X-ray tube by using at least one magnetic field sensor; determining a relative location with respect to the X-ray tube and the wireless detector based on the obtained at least one piece of magnetic field intensity information; and transmitting, to the mobile X-ray apparatus, information which relates to the determined relative location with respect to the X-ray tube and the wireless detector.

The determining the relative location with respect to the X-ray tube and the wireless detector may include: comparing the obtained at least one piece of magnetic field intensity information with reference magnetic field intensity information; and determining the relative location with respect to the X-ray tube and the wireless detector based on a result of the comparing.

The obtaining the at least one piece of magnetic field intensity information may include: obtaining first direction magnetic field intensity information which relates to a first direction of the magnetic field which is emitted by the X-ray tube by using a first magnetic field sensor which is connected to a first point of the wireless detector; and obtaining second direction magnetic field intensity information which relates to a second direction of the magnetic field which is emitted by the X-ray tube by using a second magnetic field sensor which is connected to a second point of the wireless detector, and the determining the relative location with respect to the X-ray tube and the wireless detector may include determining the relative location with respect to the X-ray tube and the wireless detector based on the obtained first direction magnetic field intensity information and the obtained second direction magnetic field intensity information.

The obtaining the at least one piece of magnetic field intensity information may include obtaining third direction magnetic field intensity information which relates to a third direction and fourth direction magnetic field intensity information which relates to a fourth direction of the magnetic field which is emitted by the X-ray tube by using a third magnetic field sensor which is connected to a third point of the wireless detector, and the determining the relative location with respect to the X-ray tube and the wireless detector may include determining the relative location with respect to the X-ray tube and the wireless detector based on the obtained third direction magnetic field intensity information and the obtained fourth direction magnetic field intensity information.

According to one or more exemplary embodiments, a non-transitory computer-readable recording medium has recorded thereon a program which, when executed by a computer, performs the information providing method.

According to one or more exemplary embodiments, an information providing apparatus for aligning an X-ray tube and a detector of a mobile X-ray apparatus is provided, and the information providing apparatus includes: an angle information obtainer which is configured for obtaining first angle information which relates to the X-ray tube by using a first angle measurement sensor which is connected to the X-ray tube, and for obtaining second angle information about the detector by using a second angle measurement sensor which is connected to the detector; and an output device which is configured for outputting rotation information which relates to guiding at least one from among a rotation direction and a rotation angle of the X-ray tube and a rotation direction and a rotation angle of the detector such that an angle between a first plane which is set with respect to the X-ray tube and a second plane which is set with respect to the detector is within a predetermined angle range, based on the obtained first angle information and the obtained second angle information.

Each of first angle measurement sensor and the second angle measurement sensor may include at least one from among a gyro sensor, an acceleration sensor, and a geomagnetic sensor.

The angle information obtainer may be further configured to obtain the first angle information which indicates a rotated angle and a rotated direction of the first plane with respect to a first reference axis, and to obtain the second angle information which indicates a rotated angle and a rotated direction of the second plane with respect to a second reference axis.

The information providing apparatus may further include a controller which is configured for rotating at least one from among the X-ray tube and the detector based on the outputted rotation information.

The information providing apparatus may further include: a magnetic field information obtainer which is configured for obtaining, from the detector, magnetic field intensity information which relates to a magnetic field which is emitted by the X-ray tube; and a location determiner which is configured for determining a relative location with respect to the X-ray tube and the detector by using the obtained magnetic field intensity information, wherein the output device may be further configured to output movement information which relates to guiding at least one from among a movement location of the X-ray tube and a movement location of the detector such that a first axis which is set with respect to the X-ray tube intersects a predetermined region of the detector, based on the determined relative location with respect to the X-ray tube and the detector.

The information providing apparatus may further include a controller which is configured for setting the first axis to be perpendicular to the first plane.

The magnetic field information obtainer may be further configured to obtain, from at least one magnetic field sensor which is connected to the detector, at least one piece of magnetic field intensity information, and the location determiner may be further configured to compare the obtained at least one piece of magnetic field intensity information with reference magnetic field intensity information, and to determine the relative location with respect to the X-ray tube and the detector based on a result of the comparison.

The magnetic field information obtainer may be further configured to obtain, from a first magnetic field sensor which is connected to a first point of the detector, first direction magnetic field intensity information which relates to a first direction of the magnetic field which is emitted by the X-ray tube and to obtain, from a second magnetic field sensor which is connected to a second point of the detector, second direction magnetic field intensity information which relates to a second direction of the magnetic field which is emitted by the X-ray tube, and the location determiner may be further configured to determine the relative location with respect to the X-ray tube and the detector based on the obtained first direction magnetic field intensity information and the obtained second direction magnetic field intensity information.

The location determiner may be further configured to compare the obtained first direction magnetic field intensity information with first reference magnetic field intensity information and to compare the obtained second direction magnetic field intensity information with second reference magnetic field intensity information.

The magnetic field information obtainer may be further configured to obtain, from a third magnetic field sensor which is connected to a third point of the detector, third direction magnetic field intensity information which relates to a third direction and fourth direction magnetic field intensity information which relates to a fourth direction of the magnetic field which is emitted by the X-ray tube, and the location determiner may be further configured to determine the relative location with respect to the X-ray tube and the detector based on the obtained third direction magnetic field intensity information and the obtained fourth direction magnetic field intensity information.

The location determiner may be further configured to compare the obtained third direction magnetic field intensity information with third reference magnetic field intensity information and to compare the obtained fourth direction magnetic field intensity information with fourth reference magnetic field intensity information.

The output device may be further configured to display a first figure which corresponds to the X-ray tube on a display which is connected to the mobile X-ray apparatus based on the obtained first angle information, and to display a second figure which corresponds to the detector on the display based on the obtained second angle information.

The output device may be further configured to display a first figure which corresponds to the X-ray tube and a second figure which corresponds to the detector on a display which is connected to the mobile X-ray apparatus based on the determined relative location with respect to the X-ray tube and the detector.

According to one or more exemplary embodiments, an information providing apparatus for aligning an X-ray tube and a detector of a mobile X-ray apparatus is provided, and the information providing apparatus includes: a magnetic field information obtainer which is configured for obtaining, from the detector, magnetic field intensity information which relates to a magnetic field which is emitted by the X-ray tube; a location determiner which is configured for determining a relative location with respect to the X-ray tube and the detector by using the obtained magnetic field intensity information; and an output device which is configured for outputting movement information which relates to guiding at least one from among a movement location of the X-ray tube and a movement location of the detector such that a first axis which is set with respect to the X-ray tube intersects a predetermined region of the detector, based on the determined relative location with respect to the X-ray tube and the detector.

According to one or more exemplary embodiments, a wireless detector for detecting an X-ray which is emitted from an X-ray tube of a mobile X-ray apparatus is provided, and the wireless detector includes: a magnetic field information obtainer which is configured for obtaining at least one piece of magnetic field intensity information which relates to a magnetic field which is emitted by the X-ray tube by using at least one magnetic field sensor; a location determiner which is configured for determining a relative location with respect to the X-ray tube and the wireless detector based on the obtained at least one piece of magnetic field intensity information; and a communication module which is configured for transmitting, to the mobile X-ray apparatus, information which relates to the determined relative location with respect to the X-ray tube and the wireless detector.

The location determiner may be further configured to compare the obtained at least one piece of magnetic field intensity information with reference magnetic field intensity information, and to determine the relative location with respect to the X-ray tube and the wireless detector based on a result of the comparison.

The magnetic field information obtainer may be further configured to obtain first direction magnetic field intensity information which relates to a first direction of the magnetic field which is emitted by the X-ray tube by using a first magnetic field sensor which is connected to a first point of the wireless detector, and to obtain second direction magnetic field intensity information which relates to a second direction of the magnetic field which is emitted by the X-ray tube by using a second magnetic field sensor which is connected to a second point of the wireless detector, and the location determiner may be further configured to determine the relative location with respect to the X-ray tube and the wireless detector based on the obtained first direction magnetic field intensity information and the obtained second direction magnetic field intensity information.

The magnetic field information obtainer may be further configured obtain third direction magnetic field intensity information which relates to a third direction and fourth direction magnetic field intensity information which relates to a fourth direction of the magnetic field which is emitted by the X-ray tube by using a third magnetic field sensor which is connected to a third point of the wireless detector, and the location determiner may be further configured to determine the relative location with respect to the X-ray tube and the wireless detector based on the obtained third direction magnetic field intensity information and the obtained fourth direction magnetic field intensity information.

BRIEF DESCRIPTION OF THE DRAWINGS

These and/or other aspects will become apparent and more readily appreciated from the following description of exemplary embodiments, taken in conjunction with the accompanying drawings in which:

FIG. 12 illustrates rotation information and movement information which are output by an information providing apparatus, according to an exemplary embodiment;

DETAILED DESCRIPTION

Figure 1:
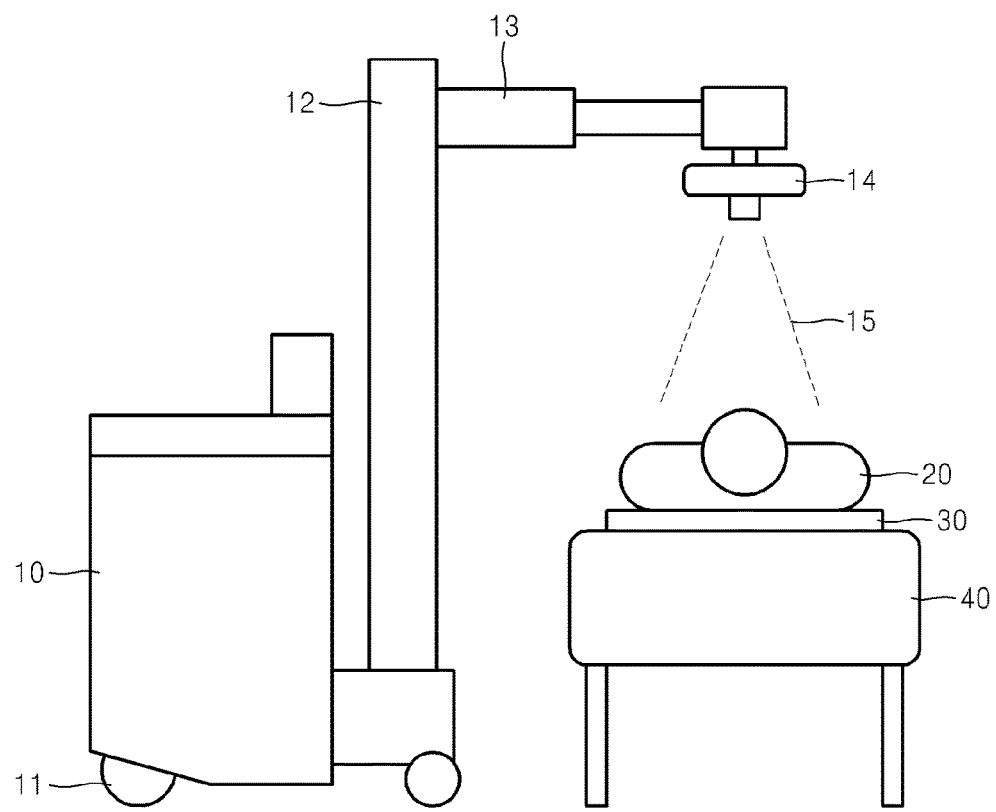
FIG. 1 is a diagram of a general mobile X-ray apparatus.

One or more exemplary embodiments will now be described more fully with reference to the accompanying drawings. The present inventive concept may, however, be embodied in many different forms and should not be construed as being limited to the exemplary embodiments set forth herein; rather, these exemplary embodiments are provided so that the present disclosure will be thorough and complete, and will fully convey the present inventive concept to those skilled in the art.

Terms used herein will now be briefly described and then one or more exemplary embodiments will be described in detail.

General terms widely used are selected while considering functions in one or more exemplary embodiments for terms used herein, but the terms used herein may differ according to intentions of one of ordinary skill in the art, precedents, or emergence of new technologies. Further, in some cases, an applicant arbitrarily selects a term, and in this case, the meaning of the term will be described in detail herein. Accordingly, the terms shall be defined based on the meanings and details throughout the specification, rather than the simple names of the terms.

When something "includes" a component, another component may be further included unless specified otherwise. The term "unit," as used in the present specification, refers to a software component, or a hardware component such as a field-programmable gate array (FPGA) or an application-specific integrated circuit (ASIC), and performs a certain function. However, the "unit" is not limited to software or hardware. The "unit" may be configured in an addressable storage medium and may be configured to be executed by one or more processors. Hence, the "unit" may include any one or more of elements such as software elements, object-oriented software elements, class elements, and task elements, and processes, functions, attributes, procedures, subroutines, segments of program codes, drivers, firmware, micro-codes, circuits, data, databases, data structures, tables, arrays, and variables. The functions provided in the elements and the units may be combined into a fewer number of elements and units or may be divided into a larger number of elements and units.

Expressions such as "at least one of," when preceding a list of elements, modify the entire list of elements and do not modify the individual elements of the list.

While describing one or more exemplary embodiments, descriptions about drawings that are not related to the one or more exemplary embodiments are omitted.

In the present specification, the term "image" may refer to multi-dimensional data which is composed of discrete image elements (e.g., pixels in a two-dimensional image and voxels in a three-dimensional image). For example, an image may include a medical image of an object which is acquired by any one or more of an X-ray, computed tomography (CT), magnetic resonance imaging (MRI), ultrasonic waves and another medical image photographing apparatus.

Furthermore, in the present specification, the term "object" may include a person or an animal, or a part of a person or an animal. For example, the object may include any one or more of the liver, the heart, the womb, the brain, a breast, the abdomen, and a blood vessel. Furthermore, the "object" may include a phantom. The phantom refers to a material having a volume that is approximately equivalent to the intensity and effective atomic number of a living thing, and may include a sphere phantom having a property which is similar to a human body.

Furthermore, in the present specification, the term "user" may refer to any one or more of a medical professional such as a doctor, a nurse, a medical laboratory technologist, and an engineer who repairs a medical apparatus, but the user is not limited thereto.

FIG. 1 is a diagram of a general mobile X-ray apparatus.

The general mobile X-ray apparatus of FIG. 1 may include a body 10, a wheel base 11, a vertical support 12, a horizontal support 13 and an X-ray tube 14.

The general mobile X-ray apparatus may move by the wheel base 11, and the X-ray tube 14 emits an X-ray 15 toward an object 20 which is arranged on a support table 40 at a location which is determined by the vertical support 12 and the horizontal support 13. A detector 30 receives the X-ray 15 that propagates through the object 20.

The X-ray 15 which is emitted from the X-ray tube 14 may be incident on the detector 30 through the object 20 in an emitted direction, or may be scattered in the object 20 and then incident on the detector 30. An X-ray (hereinafter, referred to as a first X-ray) which is incident on the detector 30 in the emitted direction from the X-ray tube 14 is necessary in order to visualize an inner structure of the object 20, but an X-ray (hereinafter, referred to as a second X-ray) which is scattered in the object 20 and then incident on the detector 30 is required to be blocked because the second X-ray deteriorates an image quality.

Figure 2:
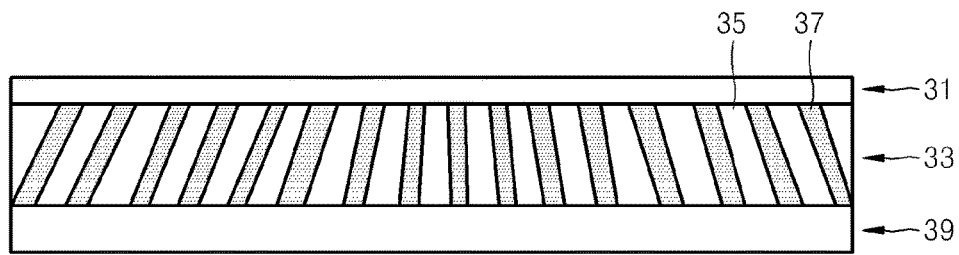
FIG. 2 is a diagram of a general detector.

FIG. 2 is a diagram of a general detector.

The general detector of FIG. 2 may include a grid cover 31, a grid 33, and a detector array unit 39.

The grid cover 31 protects the grid 33 from an external impact.

The detector array unit 39 converts a received X-ray which is emitted from an X-ray tube into an electric signal.

The grid 33 includes a plurality of X-ray transmitting strips 35 which are configured for transmitting an X-ray, and a plurality of X-ray blocking strips 37 which are configured for blocking an X-ray. The plurality of X-ray transmitting strips 35 may be arranged in a predetermined direction.

Referring back to FIG. 1, because the detector 30 is located below or behind the object 20 in the general mobile X-ray apparatus, a user of the general mobile X-ray apparatus is typically unable to accurately determine a location and an orientation of the detector 30. When the user captures an image of the object 20 while the X-ray tube 14 and the detector 30 are not accurately aligned, a first X-ray may be blocked by the X-ray blocking strips 37 and/or a second X-ray may be transmitted along the X-ray transmitting strips 35, thereby deteriorating the quality of an X-ray image.

Accordingly, it is very important in using the general mobile X-ray apparatus to align the X-ray tube 14 and the detector 30 such that the first X-ray is transmitted along the X-ray transmitting strips 35 and the second X-ray is blocked by the X-ray blocking strips 37.

Figure 3:
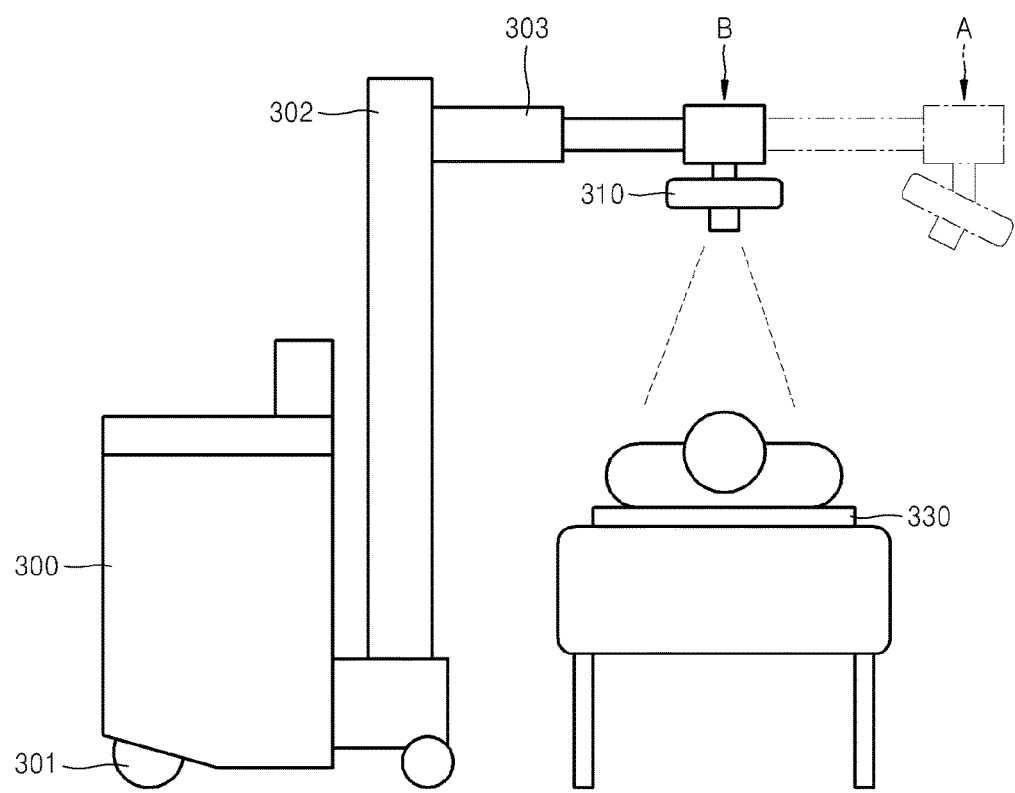
FIG. 3 is a diagram which illustrates operations of a mobile X-ray apparatus which includes an information providing apparatus, according to an exemplary embodiment.

FIG. 3 is a diagram which illustrates operations of a mobile X-ray apparatus which includes an information providing apparatus, according to an exemplary embodiment.

The mobile X-ray apparatus of FIG. 3 may include a body 300, a wheel base 301, a vertical support 302, a horizontal support 303, and an X-ray tube 310.

The body 300 controls operations of the mobile X-ray apparatus. A user may control capturing and obtaining of an X-ray image of an object by manipulating the body 300.

The wheel base 301 may enable the user to move the mobile X-ray apparatus by being connected to a bottom of the body 300.

The vertical support 302 and the horizontal support 303 connect the body 300 with the X-ray tube 310. The user may position the X-ray tube 310 at a desired location and in a desired direction by adjusting the vertical support 302 and the horizontal support 303. Structures of the vertical support 302 and the horizontal support 303 shown in FIG. 3 are only examples, and are not limited provided that the X-ray tube 310 is positioned at the desired location. For example, a robot arm having a degree of freedom in 6 axes may be connected to the body 300, instead of the vertical and horizontal supports 312 and 313.

In FIG. 3, a detector 330 is illustrated as a plane detector, but it shall be apparent to one of ordinary skill in the art that the detector 330 may have any suitable structure, including any one or more of various structures other than a plane detector.

The information providing apparatus according to an exemplary embodiment may be included in the body 300. The information providing apparatus may be configured to output information which relates to aligning the X-ray tube 310 and the detector 330 based on a relative location with respect to the X-ray tube 310 and the detector 330, and information which relates to rotation directions and rotation angles of the X-ray tube 310 and the detector 330. As shown in FIG. 3, the user may rotate the X-ray tube 310 in a counterclockwise direction while referring to the information which is output by the information providing apparatus, and the user may align the X-ray tube 310 with the detector 330 by moving the X-ray tube 310 from a point A to a point B.

Figure 4:
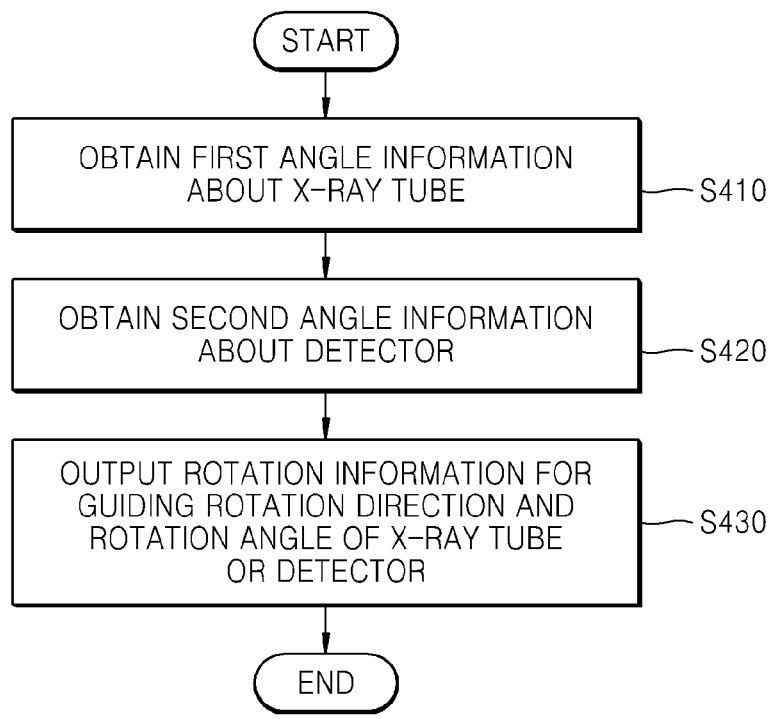
FIG. 4 is a flowchart which illustrates an information providing method, according to an exemplary embodiment.

FIG. 4 is a flowchart which illustrates an information providing method, according to an exemplary embodiment.

In operation S410, the information providing apparatus obtains first angle information which relates to the X-ray tube 310. The information providing apparatus may be configured to obtain the first angle information which is measured by a first angle measurement sensor which is connected to the X-ray tube 310.

In operation S420, the information providing apparatus obtains second angle information which relates to the detector 330. The information providing apparatus may be configured to obtain the second angle information which is measured by a second angle measurement sensor which is connected to the detector 330.

Each of the first and second angle measurement sensors may include at least one from among a gyro sensor, an acceleration sensor, and a geomagnetic sensor. Each of the first and second angle measurement sensors, according to an exemplary embodiment, may detect rotations in three axis directions, i.e., a rotation with respect to an x-y plane, a rotation with respect to a y-z plane, and a rotation with respect to a x-z plane on a three-dimensional (3D) space coordinate system including the x-axis, the y-axis, and the z-axis. Because a method for measuring a rotation direction and a rotation angle of an object which is connected to a sensor by using at least one of a gyro sensor, an acceleration sensor, and a geomagnetic sensor is well known to one of ordinary skill in the art, details thereof are not described herein.

In operation S430, the information providing apparatus outputs rotation information which relates to guiding at least one from among a rotation direction and a rotation angle of the X-ray tube 310 and/or a rotation direction and a rotation angle of the detector 330 such that an angle between a first plane which is set with respect to the X-ray tube 310 and a second plane which is set with respect to the detector 330 is within a predetermined angle range, based on the obtained first angle information and the obtained second angle information.

The first and second planes may be variously set by the user. For example, the first plane may correspond to a cross section of an X-ray which is emitted from the X-ray tube 310, and the second plane may correspond to a horizontal surface of the detector 330. Further, the predetermined angle range between the first and second planes may be variously set by the user. When the angle between the first and second planes is 0°, the first and second planes are parallel to each other.

The user may align the detector 330 and the X-ray tube 310 by adjusting the rotation direction and the rotation angle of the X-ray tube 310 and/or the rotation direction and the rotation angle of the detector 330 by using the rotation information which is output by the information providing apparatus. Accordingly, a first X-ray which is irradiated from the X-ray tube 310 may propagate through a plurality of X-ray transmitting strips which are included in a grid of the detector 330.

Alternatively, the information providing apparatus may automatically rotate the X-ray tube 310 by controlling the vertical support 302 and the horizontal support 303 of FIG. 3 based on the rotation information.

Figure 5A:
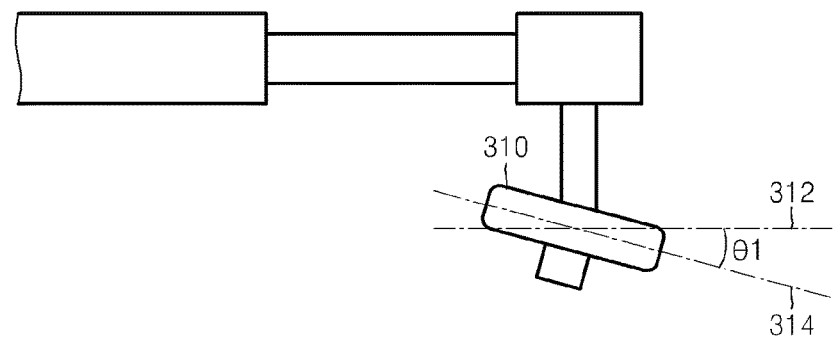
FIG. 5A is a diagram which illustrates a method for obtaining first angle information which relates to an X-ray tube.
Figure 5B:
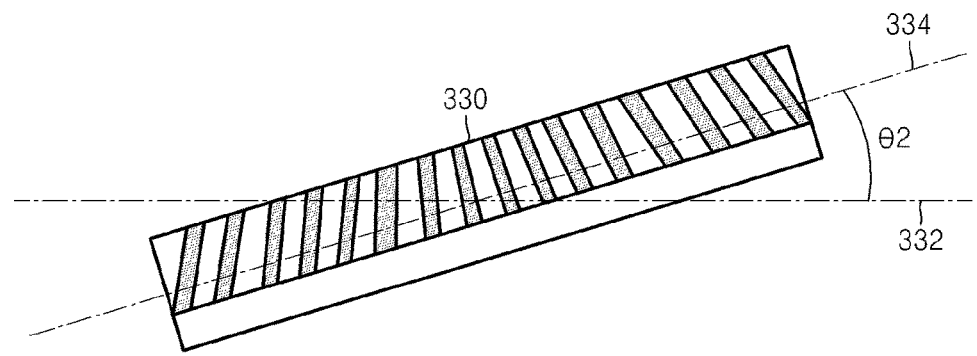
FIG. 5B is a diagram which illustrates a method for obtaining second angle information which relates to a detector.

FIG. 5A is a diagram which illustrates a method for obtaining first angle information which relates to the X-ray tube 310, and FIG. 5B is a diagram which illustrates a method for obtaining second angle information which relates to the detector 330.

In FIG. 5A, the X-ray tube 310 is connected to a first angle measurement sensor, and a first reference axis 312 is set in the first angle measurement sensor. The first reference axis 312 may include any of the x-, y-, and z-axes. The first angle measurement sensor may obtain first angle information which indicates a rotated direction and a rotated angle of a first plane 314 which is set in the X-ray tube 310 with respect to the first reference axis 312. In FIG. 5A, the first plane 314 is rotated by an angle θ1 in a clockwise direction with respect to the first reference axis 312.

In FIG. 5B, the detector 330 is connected to a second angle measurement sensor, and a second reference axis 332 is set in the second angle measurement sensor. The second reference axis 332 may include any of the x-, y-, and z-axes. The second angle measurement sensor may obtain second angle information which indicates a rotated direction and a rotated angle of a second plane 334 which is set in the detector 330 with respect to the second reference axis 332. In FIG. 5B, the detector 330 is rotated by an angle θ2 in a counterclockwise direction with respect to the second reference axis 332.

The first and second reference axes 312 and 332 may include axes that are parallel to each other, or may be variously set by the user.

As described above, the information providing apparatus may be configured to output the rotation information which relates to guiding at least one from among the rotation direction and the rotation angle of the X-ray tube 310 and/or the rotation direction and the rotation angle of the detector 330 based on the first angle information and the second angle information.

For example, when a first reference axis and a second reference axis are parallel to each other, a first plane is rotated by 30° in a clockwise direction with respect to the first reference axis, the second plane is rotated by 50° in a counterclockwise direction with respect to the second reference axis, and a predetermined angle range is from 0° to 5°, the information providing apparatus may output rotation information which relates to guiding the rotation of the X-ray tube 310 by 75° to 85° in a counterclockwise direction and/or the rotation of the detector 330 by 75° to 85° in a clockwise direction.

Figure 6:
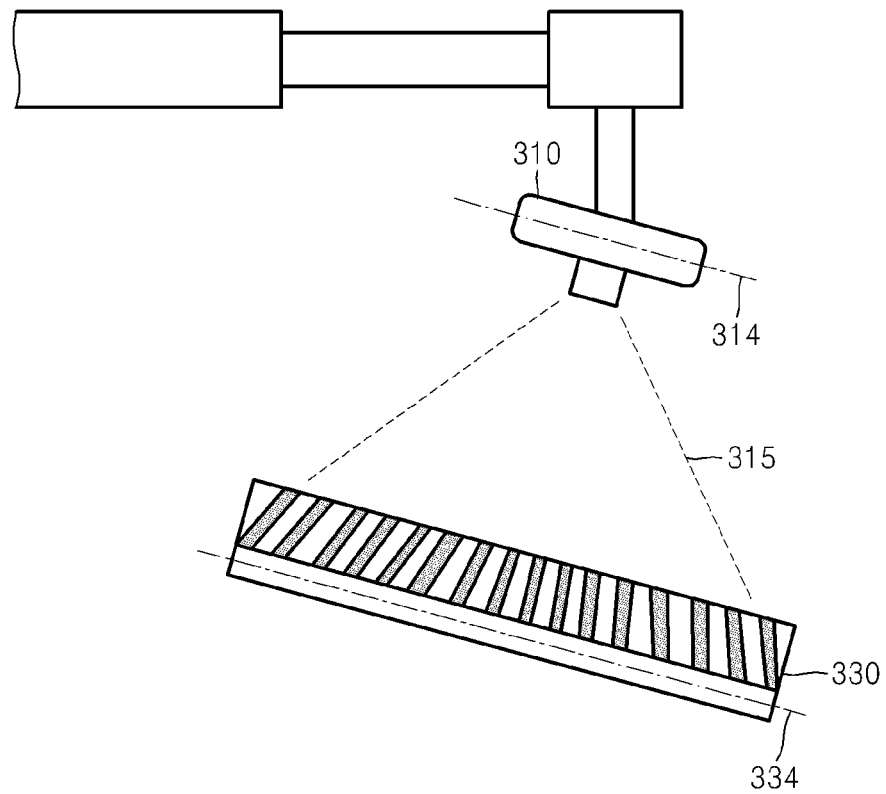
FIG. 6 is a diagram of an X-ray tube and a detector which are aligned based on rotation information which is output by an information providing apparatus, according to an exemplary embodiment.

FIG. 6 is a diagram of the X-ray tube 310 and the detector 330 which are aligned based on the rotation information which is output by the information providing apparatus, according to an exemplary embodiment. The user may align horizontal axes of the X-ray tube 310 and the detector 330 by rotating the X-ray tube 310 or the detector 330 based on the rotation information.

Figure 7:
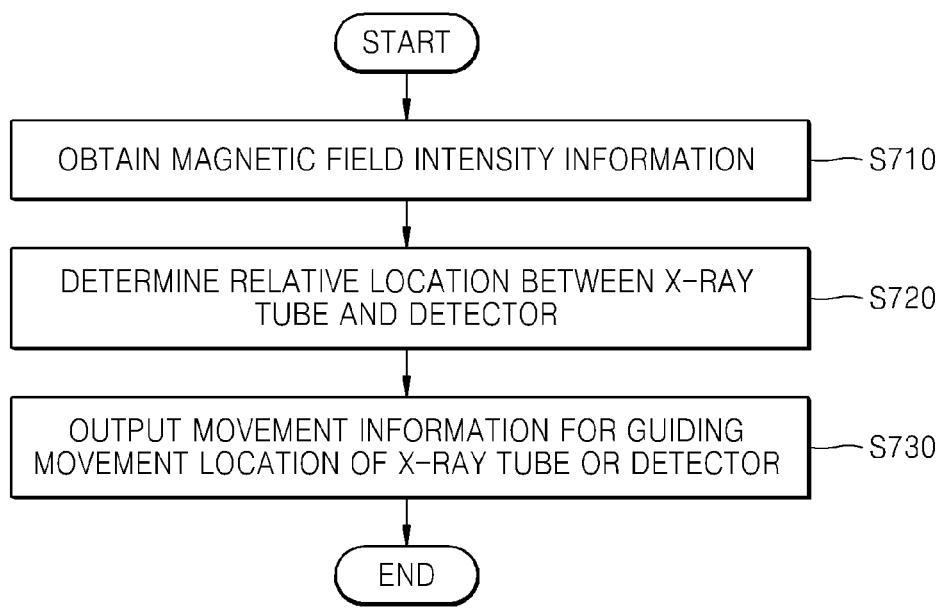
FIG. 7 is a flowchart which illustrates an information providing method, according to another exemplary embodiment.

FIG. 7 is a flowchart which illustrates an information providing method, according to another exemplary embodiment.

In operation S710, the information providing apparatus obtains magnetic field intensity information which relates to a magnetic field which is emitted by the X-ray tube 310 from the detector 330.

The information providing apparatus may be configured to i) obtain at least one piece of magnetic field intensity information from at least one magnetic field sensor which is connected to the detector 330, ii) obtain first direction magnetic field intensity information which relates to a first direction of the magnetic field from a first magnetic field sensor which is connected to a first point of the detector 330 and second direction magnetic field intensity information which relates to a second direction of the magnetic field from a second magnetic field sensor which is connected to a second point of the detector 330, or iii) obtain third direction magnetic field intensity information which relates to a third direction of the magnetic field and fourth direction magnetic field intensity information which relates to a fourth direction of the magnetic field from a third magnetic field sensor which is connected to a third point of the detector 330. Cases of i), ii), and iii) will be described below with reference to FIGS. 8, 9 and 10.

In operation S720, the information providing apparatus determines a relative location with respect to the X-ray tube 310 and the detector 330 by using the magnetic field intensity information. In detail, the information providing apparatus may be configured to determine a distance between the X-ray tube 310 and the detector 330 in any one or more of the x-, y-, and z-axis directions in a space coordinate system which includes x-, y-, and z-axes. Further, the relative location with respect to the X-ray tube 310 and the detector 330 may also include information which relates to a distance between a point in a predetermined region of the detector 330, which will be described below with reference to operation S730, and a point at which a first axis of the X-ray tube 310 and the X-ray tube 310 meet, in each of the x-, y-, and z-axis directions.

In operation S730, the information providing apparatus outputs movement information which relates to guiding at least one from among a movement location of the X-ray tube 310 and a movement location of the detector 330 such that the first axis which is set with respect to the X-ray tube 310 intersects the predetermined region of the detector 330, based on the determined relative location with respect to the X-ray tube 310 and the detector 330. The predetermined region may be set in a center portion of the detector 330, or in any location desired by the user. Further, the first axis may be variously set by the user. For example, the first axis may be a straight line which is perpendicular to a first plane which is set with respect to the X-ray tube 310 or a straight line which corresponds to a center X-ray which is emitted by the X-ray tube 310.

The horizontal axes of the X-ray tube 310 and the detector 330 are aligned according to the method illustrated in FIG. 4, whereas vertical axes of the X-ray tube 310 and the detector 330 are aligned according to the method illustrated in FIG. 7.

The magnetic field sensor, according to an exemplary embodiment, may be attached to the detector 330. In particular, if the magnetic field sensor is attached to the grid cover 31 of FIG. 2, a volume of the detector 330 may be remarkably increased, and thus the magnetic field sensor may be attached to the detector array unit 39. However, an attached region of the magnetic field sensor is not limited to the detector array unit 39. Further, the magnetic field sensor may detect a magnetic field in each of three axis directions. In particular, the magnetic field sensor may detect a magnetic field in an x-axis direction, a magnetic field in a y-axis direction, and a magnetic field in a z-axis direction.

Figure 8:
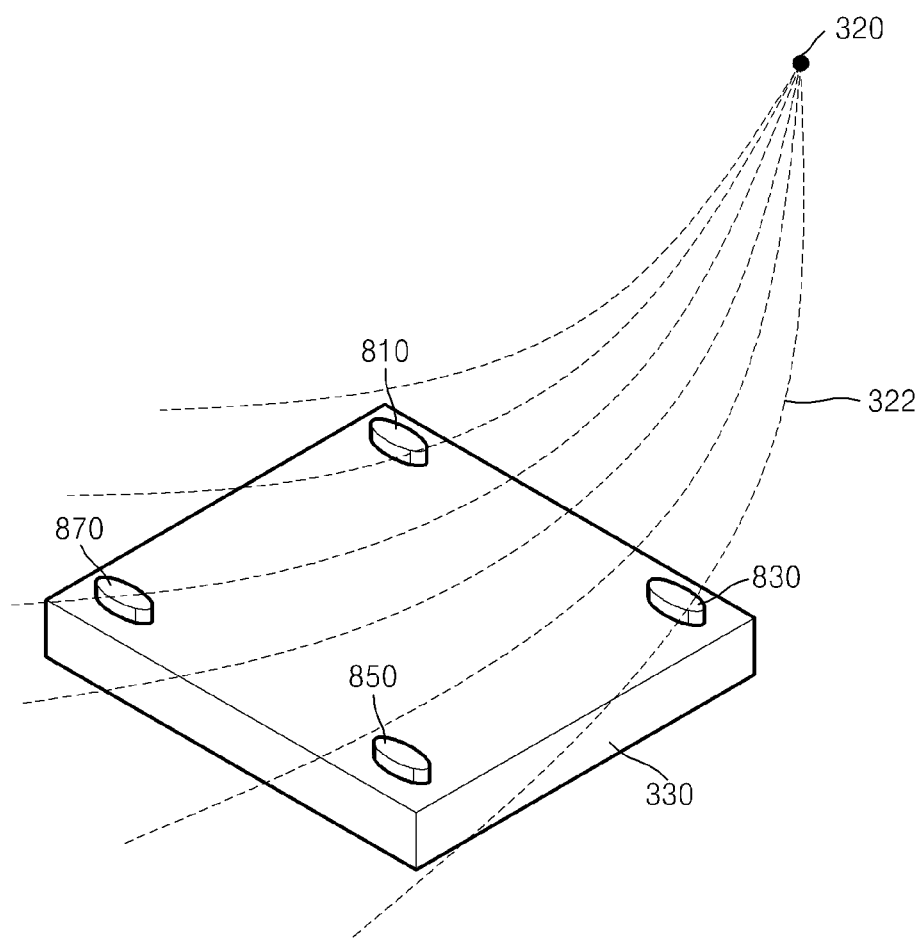
FIG. 8 is a diagram which illustrates a method for determining a relative location with respect to an X-ray tube and a detector by using four magnetic field sensors which are connected to the detector.

FIG. 8 is a diagram which illustrates a method for determining a relative location with respect to the X-ray tube 310 and the detector 330 by using first, second, third, and fourth magnetic field sensors 810, 830, 850, and 870, which are connected to the detector 330.

The first, second, third, and fourth magnetic field sensors 810, 830, 850, and 870 of FIG. 8 may be attached to respective corners of the detector 330, or to any respective location of the detector 330 which is well known to one of ordinary skill in the art. FIG. 8 illustrates four magnetic field sensors, but the number of magnetic field sensors is not limited thereto.

The X-ray tube 310 may include a magnetic field generator 320, and the magnetic field generator 320 may be configured to emit a magnetic field 322 toward the detector 330. It is assumed that locations of the magnetic field generator 320 and the X-ray tube 310 are the same.

The first, second, third, and fourth magnetic field sensors 810, 830, 850, and 870 of FIG. 8 may be configured to measure a magnetic field intensity of the magnetic field 322 which is emitted by the magnetic field generator 320.

The information providing apparatus may be configured to obtain magnetic field intensity information from each of the first, second, third, and fourth magnetic field sensors 810, 830, 850, and 870, which are attached to the detector 330, in order to determine the relative location with respect to the detector 330 and the X-ray tube 310.

In detail, because the magnetic field intensity of the magnetic field 322 is inversely proportional to a square of a respective distance between the X-ray tube 310 and each of the first, second, third, and fourth magnetic field sensors 810, 830, 850, and 870, the information providing apparatus may be configured to measure the respective distance from the X-ray tube 310 to each of the first, second, third, and fourth magnetic field sensors 810, 830, 850, and 870 by using four respective intensities which are measured by the first, second, third, and fourth magnetic field sensors 810, 830, 850, and 870, and to determine the relative location with respect to the X-ray tube 310 and the detector 330 based on the measured distances.

Alternatively, the information providing apparatus may be configured to pre-store reference magnetic field intensity information which relates to the relative location with respect to the X-ray tube 310 and the detector 330, and then to compare the four respective intensities which are measured by the first, second, third, and fourth magnetic field sensors 810, 830, 850, and 870 with the pre-stored reference magnetic field intensity information in order to determine the relative location with respect to the X-ray tube 310 and the detector 330.

Figure 9:
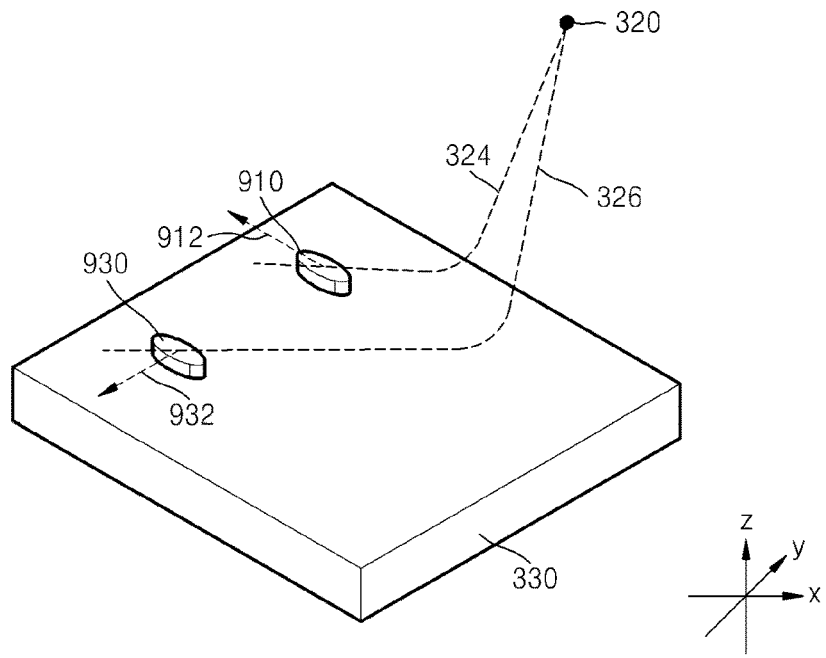
FIG. 9 is a diagram which illustrates a method for determining a relative location with respect to an X-ray tube and a detector by using two magnetic field sensors which are connected to the detector.

FIG. 9 is a diagram which illustrates a method for determining a relative location with respect to the X-ray tube 310 and the detector 330 by using fifth and sixth magnetic field sensors which are connected to the detector 330. FIG. 9 illustrates only two lines of magnetic force which are emitted from the magnetic field generator 320 for convenience of understanding.

The fifth magnetic field sensor 910 may be configured to measure a first magnetic field intensity which relates to a first direction 912 of a magnetic field 324 which is emitted from the magnetic field generator 320, and the sixth magnetic field sensor 930 may be configured to measure a second magnetic field intensity which relates to a second direction 932 of a magnetic field 326 which is emitted from the magnetic field generator 320.

In detail, the information providing apparatus sets the first and second directions 912 and 932 respectively for the fifth and sixth magnetic field sensors 910 and 930, and obtains first magnetic field intensity information which relates to the first direction 912 and second magnetic field intensity information which relates to the second direction 932 of the magnetic field which is emitted from the magnetic field generator 320 at a predetermined location with respect to the fifth and sixth magnetic field sensors 910 and 930. The first direction 912 may be set according to an x-axis direction and the second direction may be set according to a y-axis direction.

The information providing apparatus may be configured to measure a respective distance between the X-ray tube 310 and each of the fifth and sixth magnetic field sensors 910 and 930 by using the first magnetic field intensity information which relates to the first direction 912 and the second magnetic field intensity information which relates to the second direction 932, and to determine a relative location with respect to the detector 330 and the X-ray tube 310 by using the measured distances. When the first direction 912 is set according to the x-axis direction and the second direction 932 is set according to the y-axis direction, x and y coordinates of the X-ray tube 310 may be determined based on using a location of the detector 330 as a starting point.

Alternatively, the information providing apparatus may be configured to pre-store a first reference magnetic field intensity which relates to the first direction 912 and a second reference magnetic field intensity which relates to the second direction 932 based on a relative location with respect to the X-ray tube 310 and the detector 330. Then, the information providing apparatus may be configured to compare the first magnetic field intensity with the pre-stored first reference magnetic field intensity and to compare the second magnetic field intensity with the pre-stored second reference magnetic field intensity in order to determine a relative location with respect to the X-ray tube 310 and the detector 330.

The information providing apparatus may be further configured to output movement information which relates to guiding at least one from among a movement location of the X-ray tube 310 and a movement location of the detector 330 such that the first and second magnetic field intensities are the same as the first and second reference magnetic field intensities when the X-ray tube 310 and the detector 330 are aligned.

In addition, the first direction 912 which is set with respect to the fifth magnetic field sensor 910 may be set to be perpendicular to the magnetic field 324 which is irradiated from the magnetic field generator 320 toward the fifth magnetic field sensor 910 when the X-ray tube 310 and the detector 330 are aligned, and the second direction 932 which is set with respect to the sixth magnetic field sensor 930 may be set to be perpendicular to the magnetic field 326 which is irradiated from the magnetic field generator 320 toward the sixth magnetic field sensor 930 when the X-ray tube 310 and the detector 330 are aligned. In particular, when the X-ray tube 310 and the detector 330 are aligned, the first magnetic field intensity in the first direction 912 and the second magnetic field intensity in the second direction 932 both have a value of zero or approximately zero, and thus, the information providing apparatus may be configured to output location information which relates to guiding at least one from among a movement location of the X-ray tube 310 and a movement location of the detector 330 to a point at which both of the first magnetic field intensity and the second magnetic field intensity of the magnetic field which emitted from the magnetic field generator 320 of the X-ray tube 310 at a predetermined location have a value of zero or approximately zero.

Alternatively, the information providing apparatus may be configured to obtain third magnetic field intensity information which relates to a third direction which is set in a z-axis direction from the fifth or sixth magnetic field sensor 910 or 930. Because a third magnetic field intensity varies according to a perpendicular distance between the X-ray tube 310 and the fifth or sixth magnetic field sensor 910 or 930, the information providing apparatus may be configured to determine a z coordinate of the X-ray tube 310 based on using a location of the detector 330 as a starting point, based on the third magnetic field intensity information. Further, the information providing apparatus may be configured to compare the third magnetic field intensity with a pre-stored third reference magnetic field intensity in order to determine a distance between the detector 330 and the X-ray tube 310 in a z-axis direction.

Figure 10:
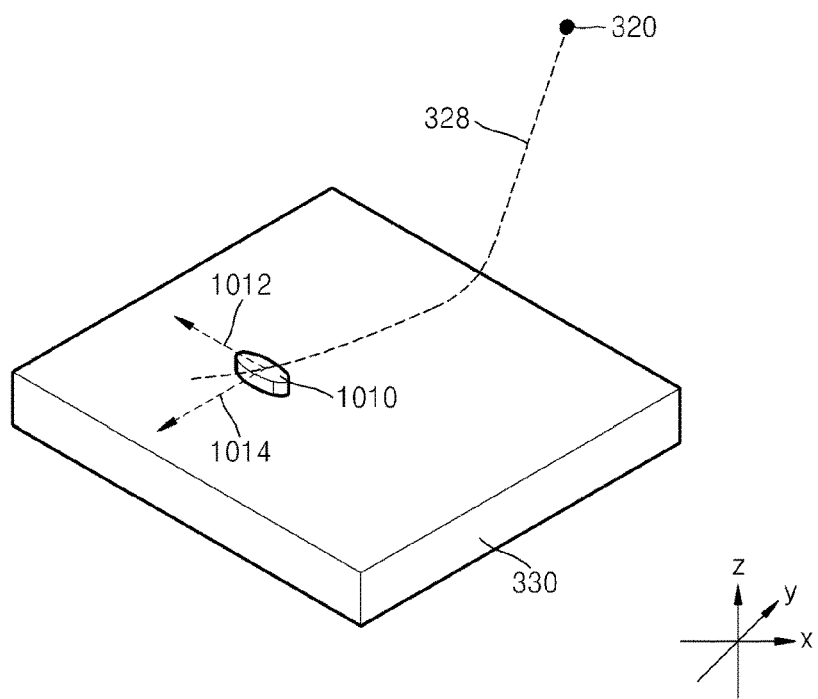
FIG. 10 is a diagram which illustrates a method for determining a relative location with respect to an X-ray tube and a detector by using one magnetic field sensor which is connected to the detector.

FIG. 10 is a diagram which illustrates a method for determining a relative location with respect to the X-ray tube 310 and the detector 330 by using a seventh magnetic field sensor 1010 which is connected to the detector 330. FIG. 10 illustrates one line of magnetic force which is emitted from the magnetic field generator 320 for convenience of understanding.

The seventh magnetic field sensor 1010 may be configured to measure a third magnetic field intensity which relates to a third direction 1012 and a fourth magnetic field intensity which relates to a fourth direction 1014 of a magnetic field 328 which is emitted from the magnetic field generator 320.

In detail, the information providing apparatus sets the third and fourth directions 1012 and 1014 with respect to the seventh magnetic field sensor 1010, and obtains third magnetic field intensity information which relates to the third direction 1012 and fourth magnetic field intensity information which relates to the fourth direction 1014 of the magnetic field which is emitted from the magnetic field generator 320 at a predetermined location with respect to the seventh magnetic field sensor 1010. The third direction 1012 may be set according to an x-axis and the fourth direction 1014 may be set according to a y-axis.

The information providing apparatus may determine a relative location with respect to the detector 330 and the X-ray tube 310 by using the third magnetic field intensity information which relates to the third direction 1012 and the fourth magnetic field intensity information which relates to the fourth direction 1014. When the third direction 1012 is set according to the x-axis and the fourth direction 1014 is set according to the y-axis, x and y coordinates of the X-ray tube 310 may be determined based on using a location of the detector 330 as a starting point.

Alternatively, the information providing apparatus may be configured to pre-store a third reference magnetic field intensity which relates to the third direction 1012 and a fourth reference magnetic field intensity which relates to the fourth direction 1014 based on a relative location with respect to the X-ray tube 310 and the detector 330. Then, the information providing apparatus may be configured to compare a third magnetic field intensity with the pre-stored third reference magnetic field intensity and compare a fourth magnetic field intensity with the pre-stored fourth reference magnetic field intensity in order to determine a relative location with respect to the X-ray tube 310 and the detector 330.

The information providing apparatus may be further configured to output movement information which relates to guiding at least one from among a movement location of the X-ray tube 310 and a movement location of the detector 330 such that the third and fourth magnetic field intensities are the same as the third and fourth reference magnetic field intensities when the X-ray tube 310 and the detector 330 are aligned.

The seventh magnetic field sensor 1010 may be positioned in the predetermined region of the detector 330 as described above with reference to operation S730 of FIG. 7, and the third direction 1012 may be set according to an x-axis direction and the fourth direction 1014 may be set according to a y-axis direction. In particular, when the X-ray tube 310 and the detector 330 are aligned, the magnetic field 328 which is irradiated toward the seventh magnetic field sensor 1010 from the magnetic field generator 320 proceeds only in a z-axis direction through the seventh magnetic field sensor 1010, and thus intensities in the x- and y-axis directions both have a value of zero or approximately zero. Accordingly, the information providing apparatus may be configured to output location information which relates to guiding at least one from among a movement location of the X-ray tube 310 and a movement location of the detector 330 to a point at which the third and fourth magnetic field intensities of the magnetic field 328 which is emitted from the magnetic field generator 320 of the X-ray tube 310 at the predetermined location have a value of zero or approximately zero.

Alternatively, the information providing apparatus may be configured to obtain fifth magnetic field intensity information which relates to a fifth direction which is set in a z-axis direction with respect to the seventh magnetic field sensor 1010. Because a fifth magnetic field intensity varies according to a vertical distance between the seventh magnetic field sensor 1010 and the X-ray tube 310, the information providing apparatus may be configured to determine a z coordinate of the X-ray tube 310 based on using a location of the detector 330 as a starting point, based on the fifth magnetic field intensity information. Further, the information providing apparatus may be configured compare the fifth magnetic field intensity with a pre-stored fifth reference magnetic field intensity in order to determine a distance between the detector 330 and the X-ray tube 310 in a z-axis direction.

Figure 11:
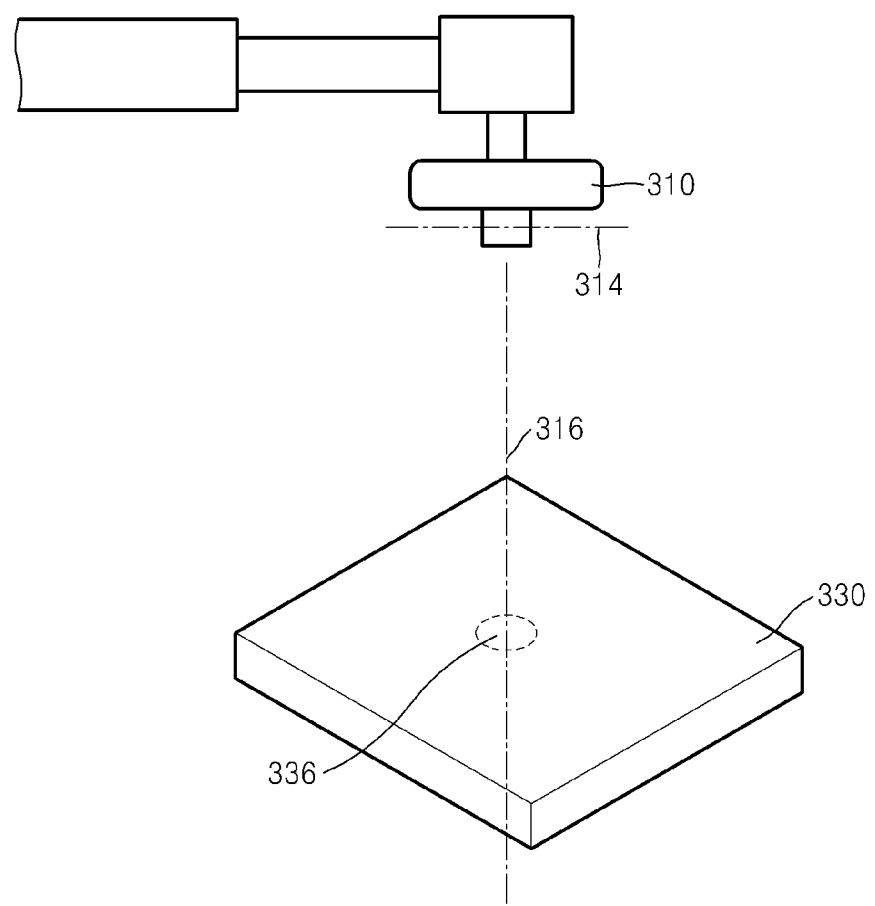
FIG. 11 is a diagram of an X-ray tube and a detector which are aligned based on location information which is output by an information providing apparatus, according to another exemplary embodiment.

FIG. 11 is a diagram of the X-ray tube 310 and the detector 330 which are aligned based on location information which is output by the information providing apparatus, according to another exemplary embodiment.

The information providing apparatus may be configured to output movement information which relates to how much the X-ray tube 310 or the detector 330 should be moved in directions which correspond to the x-, y-, and z-axes. Referring to FIG. 11, the X-ray tube 310 and/or the detector 330 is moved based on the movement information which is output by the information providing apparatus such that a first axis 316 which is set with respect to the X-ray tube 310 intersects a predetermined region 336 of the detector 330.

FIG. 12 illustrates rotation information and movement information which are output by the information providing apparatus, according to an exemplary embodiment.

The information providing apparatus may be configured to output the rotation information and the movement information by using a display which is connected to the mobile X-ray apparatus. The display may be connected to the body 300 or the X-ray tube 310 of FIG. 3. The rotation information may include information which relates to at least one from among an angle and a direction that the X-ray tube 310 and/or the detector 330 should be moved, and the movement information may include information which relates to a distance the X-ray tube 310 and/or the detector 330 should be moved in each of the x-, y-, and z-axis directions.

Figure 13A:
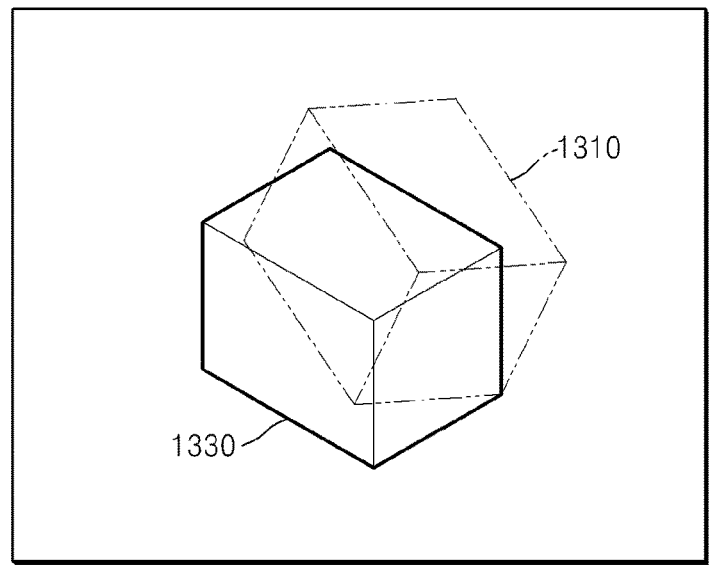
FIG. 13A illustrates rotation information which is output by an information providing apparatus, according to an exemplary embodiment.
Figure 13B:
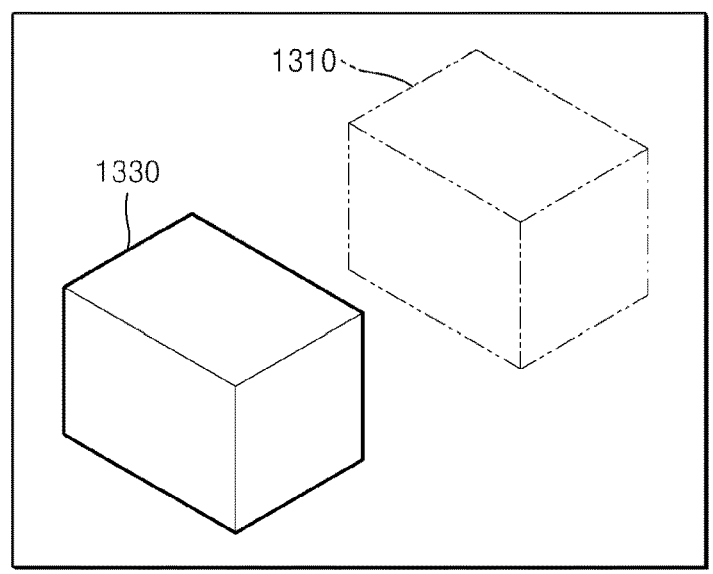
FIG. 13B illustrates movement information which is output by an information providing apparatus, according to an exemplary embodiment.

FIG. 13A illustrates rotation information which is output by the information providing apparatus, according to an exemplary embodiment, and FIG. 13B illustrates movement information which is output by the information providing apparatus, according to an exemplary embodiment.

Referring to FIG. 13A, the information providing apparatus may be configured to display a first FIG. 1310 which corresponds to the X-ray tube 310 and a second FIG. 1330 which corresponds to the detector 330 by using a display which is connected to the mobile X-ray apparatus. In particular, the information providing apparatus may be configured to display the first FIG. 1310 based on first angle information and to display the second FIG. 1330 based on second angle information.

In detail, the information providing apparatus may be configured to display the first and second FIGS. 1310 and 1330 in correspondence with a location relationship with respect to a first plane which is set in the X-ray tube 310 and a second plane which is set in the detector 330 based on the first angle information and the second angle information.

In FIG. 13A, when the first FIG. 1310 is rotated in a counterclockwise direction and/or when the second FIG. 1330 is rotated in a clockwise direction, the first and second FIGS. 1310 and 1330 may overlap each other. The information providing apparatus may be configured to overlap the first and second FIGS. 1310 and 1330 when the X-ray tube 310 and the detector 330 are aligned, and accordingly, the user may further easily align the X-ray tube 310 and the detector 330 by referring to the first and second FIGS. 1310 and 1330 which are displayed on the display.

Alternatively, referring to FIG. 13B, the information providing apparatus may be configured to display the first FIG. 1310 which corresponds to the X-ray tube 310 and the second FIG. 1330 which corresponds to the detector 330 on the display based on a relative location with respect to the X-ray tube 310 and the detector 330. In particular, the information providing apparatus may be configured to display the X-ray tube 310 and the detector 330 based on a relative location on each of the x-, y-, and z-axes. The user may easily align the X-ray tube 310 and the detector 330 by overlapping the first FIG. 1310 on the second FIG. 1330 by moving the X-ray tube 310.

Figure 14A:
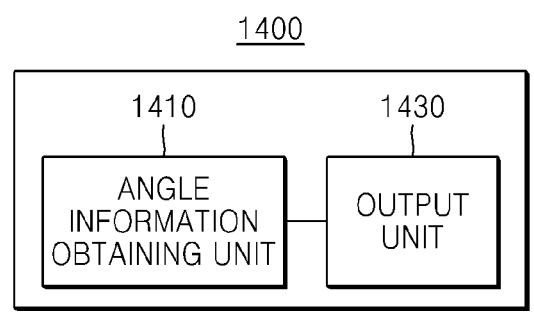
FIG. 14A is a block diagram of an information providing apparatus according to an exemplary embodiment.
Figure 14B:
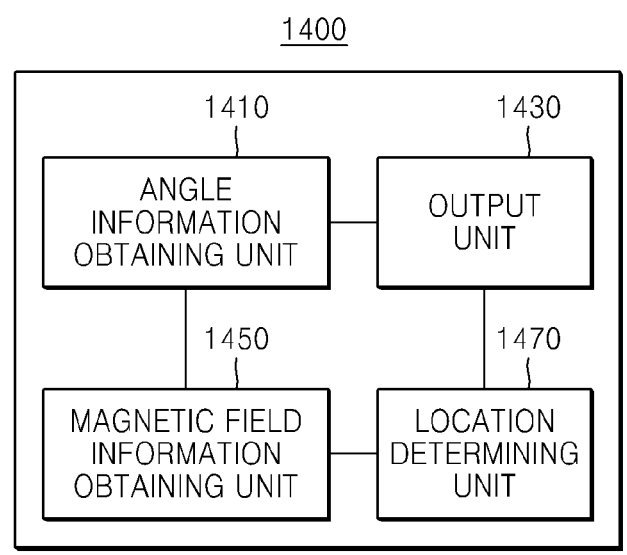
FIG. 14B is a block diagram of an information providing apparatus according to another exemplary embodiment.

FIG. 14A is a block diagram of an information providing apparatus 1400 according to an exemplary embodiment, and FIG. 14B is a block diagram of an information providing apparatus 1400' according to another exemplary embodiment.

Referring to FIG. 14A, the information providing apparatus 1400 may include an angle information obtaining unit (also referred to herein as an "angle information obtainer") 1410 and an output unit 1430. The angle information obtaining unit 1410 and the output unit 1430 may be configured as microprocessors. Further, the information providing apparatus 1400 may be included in a mobile X-ray apparatus.

The angle information obtaining unit 1410 may be configured to obtain first angle information which is measured by a first angle measurement sensor, which is connected to the X-ray tube 310. Further, the angle information obtaining unit 1410 may be configured to obtain second angle information which is measured by a second angle measurement sensor, which is also connected to the detector 330.

The output unit 1430 is configured to output rotation information which relates to guiding at least one from among a rotation direction and a rotation angle of the X-ray tube 310 and a rotation direction and a rotation angle of the detector 330 such that an angle between a first plane which is set for the X-ray tube 310 and a second plane which is set for the detector 330 is within a predetermined angle range, based on the first angle information and the second angle information. The output unit 1430 may include any one or more of a speaker, a printer, a display, and/or any other output apparatus which is well known to one of ordinary skill in the art.

Although not shown in FIG. 14A, the information providing apparatus 1400 may further include a control unit (also referred to herein as a "controller").

The control unit may control the vertical support 302 and/or the horizontal support 303 of FIG. 3 in order to control the rotation direction and/or the rotation angle of the X-ray tube 310 based on the rotation information which is output via the output unit 1430.

Referring to FIG. 14B, the information providing apparatus 1400' may include the angle information obtaining unit 1410, the output unit 1430, a magnetic field information obtaining unit (also referred to herein as a "magnetic field information obtainer") 1450, and a location determining unit (also referred to herein as a "location determiner") 1470. The angle information obtaining unit 1410, the output unit 1430, the magnetic field information obtaining unit 1450, and the location determining unit 1470 may be configured as microprocessors.

Because the angle information obtaining unit 1410 is described above with reference to FIG. 14A, details thereof are not repeated here.

The magnetic field information obtaining unit 1450 obtains magnetic field intensity information which relates to a magnetic field which is emitted by the X-ray tube 310 from the detector 330.

The location determining unit 1470 determines a relative location with respect to the X-ray tube 310 and the detector 330 by using the magnetic field intensity information. In detail, the information providing apparatus 1400 may determine a distance between the X-ray tube 310 and the detector 330 along each of the x-, y-, and z-axes in a space coordinate system which includes the x-, y-, and z-axes.

The output unit 1430 may be configured to output movement information which relates to guiding at least one from among a movement location of the X-ray tube 310 and a movement location of the detector 330 such that a first axis which is set for the X-ray tube 310 intersects a predetermined region of the detector 330 based on the relative location with respect to the X-ray tube 310 and the detector 330.

The information providing apparatus 1400' may further include a control unit (not shown) that controls the vertical support 302 and/or the horizontal support 303 of FIG. 3 in order to control the movement location of the X-ray tube 310 based on the movement information which is output via the output unit 1430.

Figure 15:
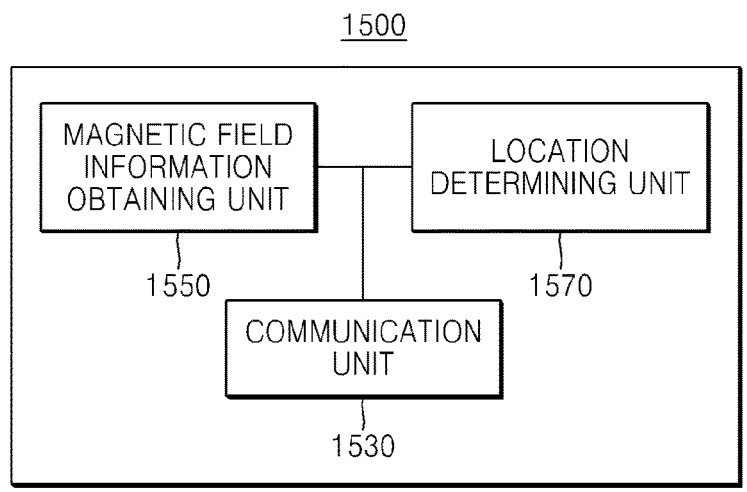
FIG. 15 is a block diagram of a wireless detector, according to an exemplary embodiment.

FIG. 15 is a block diagram of a wireless detector 1500, according to an exemplary embodiment.

Referring to FIG. 15, the wireless detector 1500 may include a magnetic field information obtaining unit 1550, a location determining unit 1570, and a communication unit (also referred to herein as a "communication module") 1530. The magnetic field information obtaining unit 1550, the location determining unit 1570, and the communication unit 1530 may be configured as microprocessors.

The magnetic field information obtaining unit 1550 obtains magnetic field intensity information which relates to a magnetic field which is emitted by the X-ray tube 310 from a magnetic field sensor which is connected to the wireless detector 1500. The magnetic field sensor may detect a magnetic field in each of three axis directions.

The location determining unit 1570 determines a relative location with respect to the X-ray tube 310 and the wireless detector 1500 by using the magnetic field intensity information.

The communication unit 1530 may be configured to perform wireless communication with a mobile X-ray apparatus, and to transmit, to the mobile X-ray apparatus, information which relates to the relative location with respect to the X-ray tube 310 and the wireless detector 1500. Further, the communication unit 1530 may be configured to receive at least one from among a rotation command and a movement command for the wireless detector 1500 from a control unit of the mobile X-ray apparatus, and to transmit the received rotation command and/or movement command to a control unit (not shown) of the wireless detector 1500 so that the control unit of the wireless detector 1500 rotates or moves the wireless detector 1500 based on the respective command.

The X-ray apparatus may be configured to output movement information which relates to guiding at least one from among a movement location of the X-ray tube 310 and a movement location of the wireless detector 1500 such that a first axis which is set for the X-ray tube 310 intersects a predetermined region of the wireless detector 1500 based on information which relates to the relative location with respect to the X-ray tube 310 and the wireless detector 1500, which information is received from the wireless detector 1500.

Figure 16:
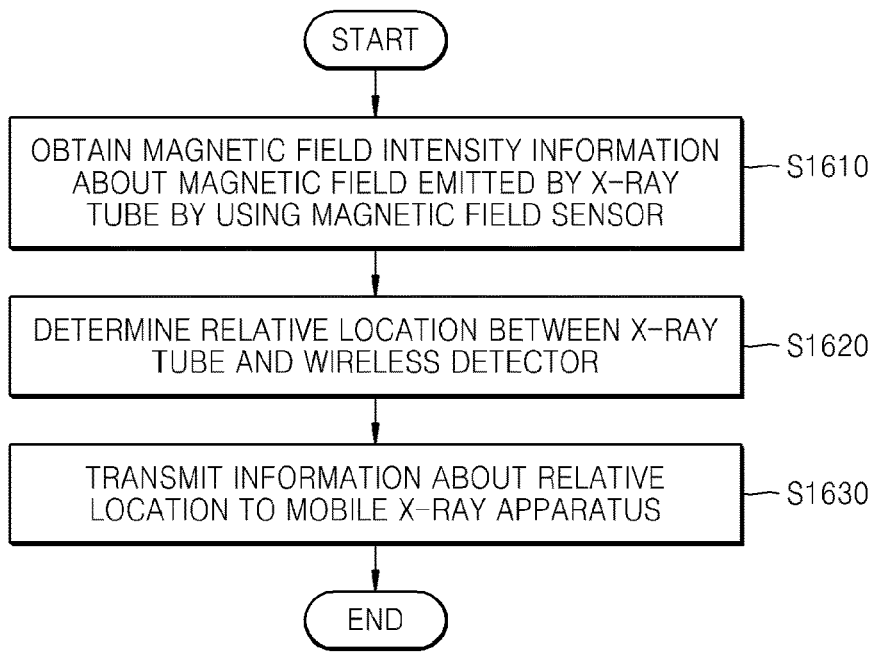
FIG. 16 is a flowchart which illustrates an information providing method, according to another exemplary embodiment.

FIG. 16 is a flowchart which illustrates an information providing method, according to another exemplary embodiment.

In operation S1610, the wireless detector 1500 obtains at least one piece of magnetic field intensity information which relates to a magnetic field which is emitted by the X-ray tube 310 by using at least one magnetic field sensor.

In operation S1620, the wireless detector 1500 determines a relative location with respect to the X-ray tube 310 and the wireless detector 1500 based on the obtained at least one piece of magnetic field intensity information.

In operation S1630, the wireless detector 1500 transmits, to a mobile X-ray apparatus, information which relates to the relative location with respect to the X-ray tube 310 and the wireless detector 1500.

The exemplary embodiments can be written as computer programs and can be implemented in general-use digital computers that execute the programs using a transitory or non-transitory computer readable recording medium.

Examples of the non-transitory computer readable recording medium include magnetic storage media (e.g., read-only memory (ROM), floppy disks, hard disks, etc.), optical recording media (e.g., compact disk-ROM (CD-ROMs), or digital versatile disks (DVDs), and/or any other suitable medium.

While one or more exemplary embodiments have been described with reference to the figures, it will be understood by those of ordinary skill in the art that various changes in form and details may be made therein without departing from the spirit and scope of the present inventive concept as defined by the following claims.

What is claimed is:

1. An information providing method for aligning an X-ray tube and a detector of a mobile X-ray apparatus, the information providing method comprising:
   obtaining first angle information which relates to the X-ray tube by using a first angle measurement sensor which is connected to the X-ray tube;
   obtaining second angle information which relates to the detector by using a second angle measurement sensor which is connected to the detector;
   detecting, by a plurality of magnetic field sensors disposed at respective corners of a surface of the detector, an intensity of a magnetic field emitted from a magnetic field generator of the X-ray tube;
   determining a relative location between the X-ray tube and the detector based on the detected intensity of the magnetic field; and
   outputting movement information relating to guiding at least one from among a movement location of the X-ray tube and a movement location of the detector based on the determined relative location with respect to the X-ray tube and the detector.

2. The information providing method of claim 1, wherein each of the first angle measurement sensor and the second angle measurement sensor comprises at least one from among a gyro sensor, an acceleration sensor, and a geomagnetic sensor.

3. The information providing method of claim 1, wherein the obtaining the first angle information comprises obtaining the first angle information which indicates a rotated angle and a rotated direction of a first plane with respect to a first reference axis, and
   the obtaining the second angle information comprises obtaining the second angle information which indicates a rotated angle and a rotated direction of a second plane with respect to a second reference axis.

4. The information providing method of claim 1,
   wherein the movement information is related to guiding at least one from among a movement location of the X-ray tube and a movement location of the detector such that a first axis which is set with respect to the X-ray tube intersects a predetermined region of the detector.

5. The information providing method of claim 1, wherein the determining the relative location with respect to the X-ray tube and the detector comprises:
   comparing at least one piece of information of the detected intensity of the magnetic field with reference magnetic field intensity information; and
   determining the relative location with respect to the X-ray tube and the detector based on a result of the comparing.

6. The information providing method of claim 1, further comprising:
   obtaining, from a first magnetic field sensor which is connected to a first point of the detector, first direction magnetic field intensity information which relates to a first direction of the magnetic field which is emitted by the X-ray tube; and obtaining, from a second magnetic field sensor which is connected to a second point of the detector, second direction magnetic field intensity information which relates to a second direction of the magnetic field which is emitted by the X-ray tube, and the determining the relative location with respect to the X-ray tube and the detector comprises determining the relative location with respect to the X-ray tube and the detector based on the obtained first direction magnetic field intensity information and the obtained second direction magnetic field intensity information.

7. The information providing method of claim 1, further comprising: obtaining, from a third magnetic field sensor which is connected to a third point of the detector, third direction magnetic field intensity information which relates to a third direction and fourth direction magnetic field intensity information which relates to a fourth direction of the magnetic field emitted by the X-ray tube, and the determining the relative location with respect to the X-ray tube and the detector comprises determining the relative location with respect to the X-ray tube and the detector based on the obtained third direction magnetic field intensity information and the obtained fourth direction magnetic field intensity information.

8. The information providing method of claim 1, wherein the outputting comprises displaying a first figure which corresponds to the X-ray tube on a display which is connected to the mobile X-ray apparatus based on the obtained first angle information, and displaying a second figure which corresponds to the detector on the display based on the obtained second angle information.

9. An information providing apparatus for aligning an X-ray tube and a detector of a mobile X-ray apparatus, the information providing apparatus comprising:

an angle information obtainer which configured to obtain first angle information which relates to the X-ray tube by using a first angle measurement sensor which is connected to the X-ray tube, and to obtain second angle information which relates to the detector by using a second angle measurement sensor which is connected to the detector;

a magnetic field information obtainer configured to obtain, by a plurality of magnetic field sensors disposed at respective corners of a surface of the detector, an intensity of a magnetic field emitted from a magnetic field generator of the X-ray tube;

a location determiner configured to determine a relative location with respect to the X-ray tube and the detector based on the detected intensity of the magnetic field; and an output device configured to output movement information relating to guiding at least one from among a movement location of the X-ray tube and a movement location of the detector based on the determined relative location between the X-ray tube and the detector, wherein the angle information obtainer, the magnetic field information obtainer, and the location determiner are included in at least one microprocessor.

10. The information providing apparatus of claim 9, wherein each of the first angle measurement sensor and the second angle measurement sensor comprises at least one from among a gyro sensor, an acceleration sensor, and a geomagnetic sensor.

11. The information providing apparatus of claim 9, wherein the angle information obtainer is further configured to obtain the first angle information which indicates a rotated angle and a rotated direction of the first plane with respect to a first reference axis, and to obtain the second angle information which indicates a rotated angle and a rotated direction of the second plane with respect to a second reference axis.

12. The information providing apparatus of claim 9, wherein the movement information is related to guiding at least one from among a movement location of the X-ray tube and a movement location of the detector such that a first axis which is set with respect to the X-ray tube intersects a predetermined region of the detector.

13. The information providing apparatus of claim 9, wherein the location determiner is further configured to compare at least one piece of information of the detected intensity of the magnetic field with reference magnetic field intensity information, and to determine the relative location with respect to the X-ray tube and the detector based on a result of the comparison.

14. The information providing apparatus of claim 9, wherein the magnetic field information obtainer is further configured to obtain, from a first magnetic field sensor which is connected to a first point of the detector, first direction magnetic field intensity information which relates to a first direction of the magnetic field which is emitted by the X-ray tube and to obtain, from a second magnetic field sensor which is connected to a second point of the detector, second direction magnetic field intensity information which relates to a second direction of the magnetic field which is emitted by the X-ray tube, and the location determiner is further configured to determine the relative location with respect to the X-ray tube and the detector based on the obtained first direction magnetic field intensity information and the obtained second direction magnetic field intensity information.

15. A method for aligning an X-ray tube with a detector of a mobile X-ray apparatus, the method comprising:

obtaining first angle information which relates to the X-ray tube by using a first angle measurement sensor which is connected to the X-ray tube;

obtaining second angle information which relates to the detector by using a second angle measurement sensor which is connected to the detector;

adjusting at least one from among a rotation direction and a rotation angle of the X-ray tube and a rotation direction and a rotation angle of the detector based on the obtained first angle information and the obtained second angle information;

obtaining, from the detector, magnetic field intensity information which relates to a magnetic field which is emitted by the X-ray tube;

determining a relative location with respect to the X-ray tube and the detector by using the obtained magnetic field intensity information; and obtaining movement information which relates to a movement of at least one from among the X-ray tube and the detector based on the determined relative location, wherein the adjusting comprises adjusting the at least one from among the rotation direction and the rotation angle of the X-ray tube and the rotation direction and the rotation angle of the detector based on the obtained movement information.

16. The method of claim 15, wherein the adjusting comprises adjusting the at least one from among the rotation direction and the rotation angle of the X-ray tube and the rotation direction and the rotation angle of the detector such that an angle between a first plane which is set with respect to the X-ray tube and a second plane which is set with respect to the detector is within a predetermined angular range.

17. The method of claim 15, wherein the obtaining the movement information comprises obtaining movement information which relates to guiding at least one from among a movement location of the X-ray tube and a movement location of the detector such that a first axis which is set with respect to the X-ray tube intersects a predetermined region of the detector.

18. An alignment apparatus for aligning an X-ray tube with a detector of a mobile X-ray apparatus, the alignment apparatus comprising:
   an angle information obtainer which is configured for obtaining first angle information which relates to the X-ray tube by using a first angle measurement sensor which is connected to the X-ray tube, and for obtaining second angle information which relates to the detector by using a second angle measurement sensor which is connected to the detector;
   a magnetic field information obtainer which is configured for obtaining, from the detector, magnetic field intensity information which relates to a magnetic field which is emitted by the X-ray tube;
   a location determiner which is configured for determining a relative location with respect to the X-ray tube and the detector by using the obtained magnetic field intensity information; and
   an output device which is configured for outputting adjustment information which relates to adjusting at least one from among a rotation direction and a rotation angle of the X-ray tube and a rotation direction and a rotation angle of the detector based on the obtained first angle information and the obtained second angle information,
   wherein the output device is further configured to output movement information which relates to a movement of at least one from among the X-ray tube and the detector based on the determined relative location, and to output adjustment information which relates to adjusting the at least one from among the rotation direction and the rotation angle of the X-ray tube and the rotation direction and the rotation angle of the detector based on the outputted movement information,
   wherein the angle information obtainer, the magnetic field information obtainer, and the location determiner are included in at least one microprocessor.

19. The alignment apparatus of claim 18, wherein the output device is further configured for outputting adjustment information which relates to the adjusting such that an angle between a first plane which is set with respect to the X-ray tube and a second plane which is set with respect to the detector is within a predetermined angular range.

20. The alignment apparatus of claim 18, wherein the output device is further configured to output movement information which relates to guiding at least one from among a movement location of the X-ray tube and a movement location of the detector such that a first axis which is set with respect to the X-ray tube intersects a predetermined region of the detector.

21. The information providing method of claim 1, further comprising:
   outputting rotation information which relates to guiding at least one from among a rotation direction and a rotation angle of the X-ray tube and a rotation direction and a rotation angle of the detector such that an angle between a first plane which is set with respect to the X-ray tube and a second plane which is set with respect to the detector is within a predetermined angle range, based on the obtained first angle information and the obtained second angle information.

22. The information providing method of claim 1, further comprising displaying a user interface including a first three-dimensional (3D) graphic item that corresponds to the X-ray tube and a second 3D graphic item that corresponds to the detector,
   wherein the first 3D graphic item and the second 3D graphic item are displayed to overlap with each other and arranged to have the rotation angle between the first 3D graphic item and the second 3D graphic item.

23. The information providing method of claim 1, wherein the surface of the detector on which the plurality of magnetic field sensors are disposed, faces the X-ray tube.

24. The information providing apparatus of claim 9, wherein the output device is further configured to output rotation information which relates to guiding at least one from among a rotation direction and a rotation angle of the X-ray tube and a rotation direction and a rotation angle of the detector such that an angle between a first plane which is set with respect to the X-ray tube and a second plane which is set with respect to the detector is within a predetermined angle range, based on the obtained first angle information and the obtained second angle information.

25. An information providing method of aligning an X-ray tube and a detector of a mobile X-ray apparatus, the information providing method comprising:
   obtaining first angle information about the X-ray tube and second angle information about the detector;
   obtaining distance information between the X-ray tube and the detector based on magnetic field intensity information about a magnetic field emitted by a magnetic field generator disposed on the X-ray tube; and
   outputting alignment guide information based on which the X-ray tube or the detector is rotated or moved so that the X-ray tube and the detector are aligned.

26. The information providing method of claim 25, wherein the outputting of the alignment guide information comprises:
   outputting rotation information for guiding at least one of a rotation direction and a rotation angle of the X-ray tube or the detector such that an angle between the X-ray tube and the detector is within a predetermined angle range based on the first angle information and the second angle information; and
   outputting movement information for guiding at least one of a movement location of the X-ray tube and a movement location of the detector such that a central axis of the X-ray tube passes through a central region of the detector, based on the distance information.

27. The information providing method of claim 25, further comprising aligning the X-ray tube and the detector by rotating or moving the X-ray tube or the detector based on the alignment guide information such that an X-ray irradiated by the X-ray tube passes through an X-ray transmitting strip included in a grid of the detector.

28. An information providing apparatus for aligning an X-ray tube and a detector of a mobile X-ray apparatus, the information providing apparatus comprising:

a processor configured to:
  obtain first angle information about the X-ray tube through a first angle measurement sensor connected to the X-ray tube and second angle information about the detector through a second angle measurement sensor connected to the detector,
  obtain, from the detector, magnetic field intensity information about a magnetic field emitted by a magnetic field generator disposed on the X-ray tube, and
  obtain distance information between the X-ray tube and the detector based on the obtained magnetic field intensity information; and
a display configured to display alignment guide information for rotating or moving the X-ray tube or the detector so that the X-ray tube and the detector are aligned.

29. The information providing apparatus of claim 28, wherein the display is further configured to display rotation information for guiding at least one of a rotation direction and a rotation angle of the X-ray tube or the detector such that an angle between the X-ray tube and the detector is within a predetermined angle range based on the first angle information and the second angle information, and movement information for guiding at least one of a movement location of the X-ray tube and a movement location of the detector such that a central axis of the X-ray tube passes through a central region of the detector based on the distance information.

30. The information providing apparatus of claim 28, further comprising an aligning unit configured to align the X-ray tube and the detector by rotating or moving the X-ray tube or the detector based on the alignment guide information such that an X-ray irradiated by the X-ray tube passes through an X-ray transmitting strip included in a grid of the detector.

* * * * *